United States Patent [19]

Fuchikami et al.

[11] Patent Number: 5,502,217

[45] Date of Patent: Mar. 26, 1996

[54] PROCESS FOR PREPARING LACTONES

[75] Inventors: Takamasa Fuchikami; Noriko Wakasa; De-Hua He, all of Sagamihara; Takanori Miyake, Yokkaichi; Takashi Okada, Yokkaichi; Atsushi Fujimura, Yokkaichi; Hiroyuki Sasakibara, Yokkaichi; Yoshiaki Kanou, Yokkaichi; Toshihiro Saito, Machida, all of Japan

[73] Assignees: Tosoh Corporation, Yamaguchi; Sagami Chemical Research Center, Tokyo, both of Japan

[21] Appl. No.: 328,607

[22] Filed: Oct. 25, 1994

Related U.S. Application Data

[63] Continuation of Ser. No. 975,326, Nov. 16, 1992, abandoned.

[30] Foreign Application Priority Data

Nov. 18, 1991 [JP] Japan ................................. 3-328381
Jun. 23, 1992 [JP] Japan ................................. 4-187465

[51] Int. Cl.$^6$ ............................................. C07D 307/33
[52] U.S. Cl. ........................................... 549/325; 549/326
[58] Field of Search ........................... 549/325, 326

[56] References Cited

U.S. PATENT DOCUMENTS

| | | | |
|---|---|---|---|
| 2,079,325 | 5/1937 | Larchar et al. | 549/325 |
| 3,994,928 | 11/1976 | Michalczyk et al. | 260/343.6 |
| 4,052,335 | 10/1977 | Michalczyk | 252/446 |
| 4,931,573 | 6/1990 | Wada et al. | 549/325 |
| 4,968,818 | 11/1990 | Bjornson et al. | 549/325 |
| 4,973,713 | 11/1990 | Manogue | 549/307 |
| 5,079,372 | 1/1992 | Wada et al. | 549/325 |

FOREIGN PATENT DOCUMENTS

| | | | |
|---|---|---|---|
| 2429085 | 1/1976 | Germany. | |
| 49-35620 | 9/1974 | Japan | 549/325 |
| 2203432 | 10/1988 | United Kingdom. | |

*Primary Examiner*—C. Warren Ivy
*Assistant Examiner*—Ba K. Trinh
*Attorney, Agent, or Firm*—Nixon & Vanderhye

[57] ABSTRACT

A lactone is prepared by catalytically hydrogenating a dicarboxylic acid having 3 to 10 carbon atoms or a functional derivative thereof in the presence of a catalyst comprising a metal selected from the elements of group VIII of the periodic table or a combination of said metal with an element selected from the elements of groups IVa, VIb and VIIb of the peridic table, and further in the co-presence of an alkali metal salt or an alkali metal hydroxide.

27 Claims, No Drawings

PROCESS FOR PREPARING LACTONES

This is a continuation of application Ser. No. 07/975,326, filed Nov. 16, 1992, now abandoned.

BACKGROUND OF THE INVENTION (1) Field of the Invention

This invention relates to a process for preparing a lactone, especially γ-butyrolactone.

γ-Butyrolactone is useful, for example, as a raw material for pyrrolidones and as a solvent for the preparation of an electrically conductive solution.

(2) Description of the Related Art

Heretofore, many proposals have been made as to the processes for preparing lactones by catalytic hydrogenation of saturated or unsaturated dicarboxylic acids or functional derivatives thereof in the liquid phase. For example, processes have been proposed which comprise using as the hydrogenation catalyst a palladium catalyst supported on active carbon (U.S. Pat. No. 3,113,138), a nickel-containing catalyst (Japanese Examined Patent Publication No. 43-6947), and a cobalt-palladium catalyst (Japanes Examined Patent Publication No. 58-29142).

In the process using a palladium catalyst supported on active carbon, when succinic anhydride is used as the raw material, γ-butyrolactone can be obtained in a high yield, but when maleic anhydride is used as the raw material, two steps are indispensable for the hydrogenation reaction and further the catalyst must be added in the midst of reaction. The process using a nickel-containing catalyst or a cobalt-palladium catalyst are advantageous from a viewpoint of the catalyst cost, but severe reaction conditions, e.g., a temperature of 250° C. and a pressure of 100 kg/cm$^2$, are usually necessary and therefore, undesirable side reactions occur which include, for example, production of cyclic ethers and decarbonilation, and selectivities to lactones are low.

SUMMARY OF THE INVENTION

A primary object of the present invention is to provide a process for preparing a lactone, especially γ-butyrolactone, wherein the intended lactone can be obtained with a high selectivity by a single hydrogenation step out under mild conditions from either any saturated or unsaturated dicarboxylic acid or functional derivative thereof.

In accordance with the present invention, there is provided a process for the preparation of a lactone which comprises catalytically hydrogenating at least one compound selected from dicarboxylic acids having 3 to 10 carbon atoms and functional derivatives thereof in the presence of a catalyst comprising at least one metal selected from the elements of group VIII of the periodic table or a combination of said metal with at least one element selected from the elements of groups IVa, VIb and VIIb of the periodic table, and further in the co-presence of an alkali metal salt and/or an alkali metal hydroxide.

DESCRIPTION OF THE PREFERRED EMBODIMENTS

The starting compounds used for the hydrogenation process of the invention are dicarboxylic acids having 3 to 10 carbon atoms and functional derivatives thereof such as anhydrides and esters. As the dicarboxylic acids, there can be mentioned, for example, maleic acid, succinic acid, fumaric acid, itaconic acid, citraconic acid, mesaconic acid, methylsuccinic acid and glutaric acid. As the functional derivatives thereof, there can be mentioned, for example, anhydrides such as maleic anhydride, succinic anhydride, itaconic anhydride, citraconic anhydride, methylsuccinic anhydride and glutaric anhydride, and esters such as methyl maleate, ethyl maleate, butyl maleate, methyl succinate, ethyl succinate and butyl succinate. Especially, in the case where γ-butyrolactone is prepared, maleic anhydride, maleic acid, succinic anhydride, succinic acid and fumaric acid are preferably used. Provided that the intended hydrogenated product is the same, two or more of these starting compounds may be used in combination in any ratio.

The dicarboxylic acids and functional derivatives thereof are preferably used for the hydrogenation reaction in the form of a solution in a solvent. The solvent used is selected from those which are inert to the hydrogenation reaction and incapable of reacting with the lactone produced. As the solvent, there can be mentioned, for example, ethers such as diethyl ether, dimethoxyethane, diglyme, triglyme, tetrahydrofuran and dioxane, esters such as methyl acetate, ethyl acetate, methyl benzoate and ethyl benzoate, alcohls such as methanol, ethanol, n-butanol, iso-butanol, tert.-butanol and 1,4-butanediol, aliphatic hydrocarbons such as n-hexane and cyclohexane, acids such as acetic acid, lactones such as γ-butyrolactone, and acid amides such as 2-pyrrolidone and N-methylpyrrolidone. Of these solvents, dimethoxyethane and tetrahydrofuran are preferable because these solvents have a relatively low boiling point and are easy to recover. Also, γ-butyrolactone is preferable because there is no need of recovery.

The amount of the solvent is not particularly limited, provided that the starting compound used is soluble therein at the reaction temerature. The solvent need not be completely dried and may contain a minor amount, i.e., usually up to one molar equivalent, of water.

The catalyst used is at least one metal selected from group VIII of the periodic table or a combination of said metal with at least one element selected from groups IVa, VIb and VIIb of the periodic table. These catalysts may be supported on a carrier.

As the metal of group VIII of the periodic table, there can be mentioned, for example, iron, cobalt, nickel, ruthenium, rhodium, palladium, iridium and platinum.

These metal catalysts are prepared from compounds containing the metal of group VIII of the periodic table, which can be converted to metal prior to or during the hydrogenation reaction. The metal-containing compounds include, for example, inorganic compounds such as chloride, nitrate, sulfate and oxide of the metal of group VIII of the periodic table, organic compounds such as acetate and acetylacetonate of said metal, and complexes such as an ammine complex and carbonyl complex of said metal.

Taking palladium as example of the metal of group VIII of the periodic table, the metal-containing compounds include, for example, inorganic palladium compounds such as ammonium hexachloropalladate, ammonium tetrachloropalladate, palladium bromide, palladium chlorocarbonyl, palladium chloride, palladium iodide, palladium nitrate, palladium oxide and palladium sulfate, organic palladium compounds such as palladium acetate, and palladium complexes such as tetraammine palladium chloride, tetraammine palladium nitrate, cis-dichlorodiamine palladium, trans-dichlorodiamine palladium, dichloro(ethylenediamine) palladium and potassium tetracyanopalladate.

The above-mentioned metal catalyst may be used in combination with at least one element selected from the elements of group IVa, VIb and VIIb of the periodic table. The elements of group IVa of the periodic table include, for example, lead, the elements of group VIb of the periodic table include, for example, chromium, molybdenum and tungsten, and the elements of group VIIb of the periodic table include, for example, rhenium.

The elements of groups IVa, VIb and VIIb of the periodic table are prepared from compounds containing these elements. As specific examples of the compounds containing an element of group IVa, there can be mentioned lead-containing compounds such as lead acetate, lead bromide, lead carbonate, lead chloride, lead iodide, lead nitrate, lead oxide, lead perchlorate, lead sulfate, lead oxalate and lead tartrate. As specific examples of the compounds containing an element of group VIb, there can be mentioned molybdenum-containing compounds such as ammonium molybdate, molybdenum acetate and molybdenum hexacarbonyl. As specific examples of the compounds containing an element of group VIIb, there can be mentioned rhenium-containing compounds such as rhenium chloride, rhenium oxide, perrhenic acid and ammonium perrhenate.

When the catalyst is supported on a carrier, the amount of the metal of the group VIII supported is preferably 0.1 to 60% by weight, more preferably 0.5 to 50% by weight, based on the total weight of the catalyst comprising the metal of the group VIII and the carrier. If the amount of the metal of the group VIII exceeds 60% by weight, the increase in the catalytic activity per unit weight of the metal catalyst is low. If the amount of the metal of the group VIII is lower than 0.1% by weight, the total catalytic activity is low.

When the catalyst used is composed of the metal of group VIII of the periodic table and at least one element selected from groups IVa, VIb and VIIb of the periodic table, the atomic ratio of the metal of the group VIII to the element of the groups IVa, VIb and VIIb is in the range of 200/1 to 1/50, preferably 100/1 to 1/20.

The procedure by which the catalyst supported on a carrier is prepared is not particularly limited, and the supported catalyst can be prepared by a conventional procedure, which includes, for example, a precipitation, kneading, impregnation, ion-exchange or deposition method.

For example, when the supported catalyst is prepared by an impregnation method, a compound containing a metal of the group VIII and an optional compound containing at least one element of the group IVa, VIb or VIIb are dissolved in an appropriate solvent, and a carrier is incorporated in the solution. If desired, the solution is allowed to stand for a predetermined period, and then, dried. The thus-dried product can be reduced into the catalyst either directly or after calcination. Alternatively, the dried product can be reduced during the reaction of hydrogenating a dicarboxylic acid or a functional derivative thereof to a lactone.

The manner in which the dried product is reduced is not particularly limited provided that a metal of the group. VIII which has a valency of substantially zero can be obtained. For example, the dried product can be reduced in the gas or vapor phase using, e.g., hydrogen or in the liquid phase using, e.g., a hydrazine. The reducing temperature is not particularly limited provided that the metal compound used is reduced to a valency of substantially zero, and is usually up to 600° C. When the metal of the group VIII is used in combination with at least one element selected from the groups IVa, VIb and VIIb, the valency of the element selected from the groups IVa, VIb and VIIb is not particularly limited. This element may be of a valency of zero or in an oxidized state after the metal compound of the group VIII is reduced to a valency of substantially zero.

When the supported catalyst is prepared by an ion-exchange of hydroxyl groups of the carrier with a compound of a metal of the group VIII and an optional compound of at least one element selected from the groups IVa, VIb and VIIb., the compound of a metal of the group VIII and the optional compound of an element of the groups IVa, VIb and VIIb are subjected to an ion-exchange, and the ion-exchanged product is treated in a manner similar to that in the above-mentioned impregnation method.

When the supported catalyst is prepared by a deposition method, a compound of a metal of the group VIII and an optional compound of at least one element selected from the groups IVa, VIb and VIIb are dissolved in an appropriate solvent, e.g., water, a carrier is added in the solution, a precipitating agent is introduced gradually or at once into the solution with stirring to deposit the respective components onto the carrier, and the resulting precipitate mixture is dried and then treated in the same manner as described in the above-mentioned impregnation method.

The catalyst components can be supported on a carrier either at once or consecutively.

The carrier used for supporting the catalyst thereon is not particularly limited provided that the catalyst is porous and capable of supporting the catalyst thereon. Specific examples of the carrier are crystalline or non-crystalline metal oxides and double oxides such as silica, alumina, magnesia, titania, silica-alumina, silica-magnesia, zeolite, diatomaceous earth, clay compounds such as teniorite, hectorite, montmorillonite and bentonite, and active carbon. Of these, silica and active carbon are preferable.

The configuration of the catalyst is not particularly limited, and the catalyst can be used as it is in a powder form or after it is molded, according to the reaction procedure and apparatus. Usually, a powder or a granule is used in a suspension bed reactor, and a shaped article of a tablet or a spherical form or extruded article from a tablet is used in a fixed bed reactor.

The amount of the catalyst used is not particularly limited, and is preferably in the range of from 0.5 to 200% by weight, more preferably from 1 to 150% by weight, based on the total weight of the reactants to be hydrolyzed.

In the hydrogenation process of the invention, an alkali metal salt and/or an alkali metal hydroxide is used together with the hydrogenation catalyst of a metal of group VIII of the periodic table or a combination of a metal with at least one element selected from the groups of IVa, VIb and VIIb thereof. The alkali metals are those which appear in group Ia of the periodic table, and include, for example, lithium, sodium, potassium, rubidium and cesium.

As the alkali metal salts, there can be mentioned alkali-type zeolites, inorganic alkali metal salts, alkali metal salts of a monofunctional organic compound, organic cation exchange materials, the cation of which has been exchanged with an alkali metal, and alkali metal salts of an organic compound having at least two functional groups. These alkali metal salts can be used either alone or in combination.

By the term "alkali-type zeolites" used herein we mean zeolites containing an alkali metal cation as the ion-exchangeable cation. The zeolites used may be of any skeletal structure. As specific examples of the alkali-type zeolites, there can be mentioned, for example, natural zeolites such as gmelinite, erionite, offretite, mazzite, mordenite and ferrierite, which have as an ion-exchangeable cation an alkali cation such as sodium, potassium, rubidium or cesium, and synthetic zeolites such as A-type, X-type, Y-type, USY-type (which may be called as US-Y-type), L-type and ZSM-5 zeolites, which have an alkali cation such as mentioned above.

Another example of the alkali metal salts is an inorganic alkali metal salt. The inorganic alkali metal salt includes various inorganic salts of an alkali metal such as lithium, sodium, potassium, rubidium or cesium. As examples of the inorganic alkali metal salts, there can be mentioned a chloride, nitrate, nitrite, carbonate, sulfate, phosphate and hydroxide of the above-mentioned alkali metals. Clay compounds which contain an alkali metal can also be used. As specific examples of the inorganic alkali metal salts, there can be mentioned chlorides such as lithium chloride, sodium chloride, potassium chloride, rubidium chloride and cesium chloride, nitrates such as lithium nitrate, sodium nitrate, potassium nitrate, rubidium nitrate and cesium nitrate, nitrites such as lithium nitrite, sodium nitrite, potassium nitrite, rubidium nitrite and cesium nitrite, carbonates such as lithium carbonate, sodium carbonate, potassium carbonate, rubidium carbonate and cesium carbonate, sulfates such as lithium sulfate, sodium sulfate, potassium sulfate, rubidium sulfate and cesium sulfate, phosphates such as lithium phosphate, sodium phosphate, potassium phosphate, rubidium phosphate and cesium phosphate, and hydroxides such as sodium hydroxide, potassium hydroxide, rubidium hydroxide and cesium hydroxide. Sodium-type, potassium-type, rubidium-type and cesium-type montmorillonite and kaolinite are also mentioned.

Still another example of the alkali metal salts is alkali metal salts of a monofunctional organic compound. The alkali metal salts of a monofunctional organic compound include, for example, alkali metal salts of a monofunctional aliphatic acid such as an acetate, a trifluoroacetate, a propionate and a methylsulfonate, and alkali metal salts of a monofunctional aromatic acid such as a benzoate, a benzenesulfonate and a p-toluenesulfonate. As specific examples of the alkali metal salts of a monofunctional aliphatic acid, there can be mentioned acetates such as lithium acetate, sodium acetate, potassium acetate, rubidium acetate and cesium acetate, trifluoroacetates such as lithium trifluoroacetate, sodium trifluoroacetate, potassium trifluoroacetate, rubidium trifluoroacetate and cesium trifluoroacetate, propionates such as lithium propionate, sodium propionate, potassium propionate, rubidium propionate and cesium propionate, and methylsulfonates such as lithium methylsulfonate, sodium methylsulfonate, potassium methylsulfonate, rubidium methylsulfonate and cesium methylsulfonate. As specific examples of the alkali metal salts of a monofunctional aromatic acid, there can be mentioned benzoates such as lithium benzoate, sodium benzoate, potassium benzoate, rubidium benzoate and cesium benzoate, benzenesulfonates such as sodium benzenesulfonate, potassium benzenesulfonate, rubidium benzenesulfonate and cesium benzenesulfonate, and p-toluenesulfonates such as sodium p-toluenesulfonate, potassium p-toluenesulfonate, rubidium p-toluenesulfonate and cesium p-toluenesulfonate.

The organic ion exchange materials are functional substances made of a high polymeric matrix material having functional groups, and include, for example, ion exchange resins, ion exchange fibers and ion exchange membranes. As specific examples of the polymeric matrix materials for these organic ion exchange materials, there can be mentioned, for example, a methacrylic acid-divinylbenzene copolymer, an acrylic acid-divinylbenzene copolymer, a styrene-divinylbenzene copolymer having functional groups in the side chains, a phenol-formaldehyde copolymer having functional groups in the side chains, and a perfluorovinyl-ether-tetrafluoroethylene copolymer.

In the styrene-divinylbenzene copolymer, the benzene ring having ion exchange groups may have introduced thereon an electron withdrawing group such as a halo, nitro, carboxyl or acyl group for the enhancement of thermal stability.

The divinylbenzene copolymers are usually cross-linked. The smaller the degree of crosslinking, i.e., the content of a crosslinking agent, the larger the size of micropores formed within the cation exchange material. In other words, the larger the degree of crosslinking, the smaller the size of the micropores and the higher the density of the cation exchange resin. A typical example of the divinylbenzene copolymers contains 6 to 20% by weight of divinylbenzene and has a crosslinking degree of about 8%. But, the divinylbenzene copolymers used in the invention are not particularly limited thereto.

The functional groups possessed by the polymeric matrix material of the organic ion exchange material, i.e., the styrene-divinylbenzene copolymer or the phenolformaldehyde copolymer, are acidic functional groups used for the cation exchange and include, for example, a sulfonic acid group, a carboxyl group, a phosphonic acid group, a phosphinic acid group and an arsenic acid group. The organic ion exchange materials can be classified into a gel type and a macroporous type from a standpoint of physical properties. The gel type is generally transparent and homogeneous spherical particles which are formed by a suspension polymerization. The macroporous type is composed of a matrix material having relatively large pores which are formed by a suspension polymerization using a specific organic solvent. The macroporous type includes a macro-reticular type ion exchange material having a macro-network structure formed from an aggregate of microspheres and having micropores of a diameter of some tens of angstroms. The organic ion exchange materials used in the invention may be any of the gel type and the macroporous type.

The organic cation exchange materials are usually available in the form of a proton type or an alkali metal type. The alkali metal type can be used as it is, and the proton type can be used after ion-exchange with a desired alkali cation. The method of ion-exchange of the proton type with a desired alkali cation is not particularly limited. For example, there can be mentioned a method of letting an aqueous solution of an alkali metal salt flow through a column packed with a cation exchange material, and a batchwise method wherein a cation exchange material and an aqueous solution of an alkali metal salt are contacted with each other in a vessel. Thus-treated materials are washed with water and then dried to give an alkali metal cation exchange material. The drying of the treated materials can be conducted at a temperature varying depending upon the particular thermal resistance of the cation exchange materials, and if desired, under a reduced pressure. The degree of ion exchange is preferably at least 50% because insufficient degree of ion exchange sometimes does not bring about the intended effect.

A further example of the alkali metal salts is an alkali metal salt of an organic compound having at least two functional groups. The organic compound having at least two functional groups is an aliphatic or aromatic compound which has as one of the functional groups a carboxyl group or a sulfonic group and as the other functional group or groups at least one functional group selected from a hydroxyl group, a carboxyl group, an alkoxycarbonyl group having 1 to 10 carbon atoms in the alkyl group, a formyl group, a sulfonic acid group and an amino group. As specific examples of the organic compound having at least two functional groups, there can be mentioned dicarboxylic acids such as maleic acid, succinic acid, oxalic acid, glutaric acid and phthalic acid, dicarboxylic acid monoesters such as monomethyl maleate, monoethyl succinate, monoethyl oxalate and monopropyl glutarate, hydroxycarboxylic acids such as 4-hydroxybutyric acid, 3-hydroxybutyric acid and salicylic acid, amino carboxylic acids such as amino benzoic acid, 2-amino isobutyric acid and 5-amino valeric acid, formyl carboxylic acids such as formyl benzoic acid, 4-formyl cinnamic acid and 3-formyl propionic acid, sulfocarboxylic acids such as sulfoacetic acid and 5-sulfoisophthalic acid, hydroxysulfonic acids such as p-hydroxybenzenesulfonic acid and 2-hydroxyethane-1-sulfonic acid, amino sulfonic acids such as 2-aminoethane-1-sulfonic acid and 3-amino-2-(4-chlorophenyl)-propylsulfonic acid, formyl sulfonic acids such as 2-formyl benzenesulfonic acid, sulfocarboxylic acid esters such as methyl sulfoacetate and methyl 5-sulfoisophthalate, disulfonic acids such as m-benezenedisulfonic acid, sulfohydroxy-carboxylic acids such as 5-sulfosalicylic acid, and hydroxyamino carboxylic acids such as 2-hydroxy-4-amino-benzoic acid.

The functional groups contained in the above-mentioned organic compound may be partly or wholly in the form of an alkali metal salt. As preferred examples of the alkali metal salt of the organic compound having at least two functional groups, there can be mentioned maleic acid salts such as sodium maleate, potassium maleate, rubidium maleate, cesium maleate, monosodium maleate, monopotassium maleate, monorubidium maleate and monocesium maleate, succinic acid salts such as sodium succinate, potassium succinate, rubidium succinate, cesium succinate, monosodium succinate, monopotassium succinate, monorubidium succinate and monocesium succinate, and hydroxycarboxylic acid salts such as potassium 4-hydroxybutyrate, rubidium 4-hydroxybutyrate and cesium 4-hydroxybutyrate.

As the alkali metal hydroxide, there can be mentioned lithium hydroxide, sodium hydroxide, potassium hydroxide, rubidium hydroxide and cesium hydroxide.

The amount of the alkali metal salt and/or the alkali metal hydroxide is not particularly limited, but is usually 0.1 to 100% by weight, preferably 1 to 50% by weight, based on the weight of the reactants to be hydrogenated. If the amount of the alkali metal salt is too large, an undesirably large reaction apparatus is necessary and, when the reaction is effected in a suspended bed, removal of the alkali metal salt and/or the alkali metal hydroxide after the reaction is troublesome. If the amount of the alkali metal salt is too small, the intended satisfactory yield cannot be obtained.

The hydrogenation reaction of the invention can be carried out either in a batchwise, semi-batchwise or continuous manner using a suspended bed, or in a manner wherein reactants are allowed to flow through a fixed bed.

The hydrogenation reaction of the invention is carried out at an elevated temperature in a hydrogen atmosphere under pressure. The reaction temperature is in the range of room temperature to 300° C., preferably 50° to 250° C. If the reaction temperature is higher than 300° C., side reactions occur to a large extent. If the reaction temperature is too low, the rate of reaction becomes undesirably low. The pressure of hydrogen is in the range of 10 to 200 kg/cm$^2$G, preferably 20 to 150 kg/cm$^2$G. The satisfactory rate of reaction can be obtained with this pressure range, and therefore, a higher pressure over 200 kg/cm$^2$G is not needed. If the hydrogen pressure is too low, the rate of reaction is undesirably low.

Although the reaction time varies depending upon the particular temperature, pressure, amount of the catalyst and reaction procedure, and, is not decided unequivocally where the reaction is carried out in a batchwise or semi-batchwise manner, the reaction time is at least one hour, preferably 1 to 20 hours. Within this period of time, the reaction is usually completed. When the reaction time is shorter than one hour, the conversion is occasionally undesirably low. Where the reaction is carried out in a continuous manner using a suspended bed or in a manner wherein reactants are allowed to flow through a fixed bed, the residence time is usually in the range of 0.1 to 10 hours.

The invention will now be described more specifically by the following examples that by no means limit the scope of the invention.

EXAMPLE 1

In 40 ml of 2N hydrochloric acid, 0.44 g of palladium chloride (PdCl$_2$) was dissolved. Into this solution, 4.94 g of powdery active carbon having a particle diameter below 200 mesh was added. Water was removed from the solution under a reduced pressure by using a rotary evaporator, and the paste obtained was dried under a reduced pressure at 80° C. for 2 hours and further at 110° C. for 2 hours. Thus-obtained catalyst precursor was introduced into a tubular glass, and was reduced under the flow of a mixed gas composed of 100 ml/min of nitrogen and 10 ml/min of hydrogen at 400° C. for 2 hours to give a palladium catalyst containing 5% by weight of palladium supported on active carbon (hereinafter abbreviated to "5% Pd/C").

A stainless steel autoclave having a volume of 10 ml was charged with 98 mg (1 m-mol) of maleic anhydride, 21 mg of 5% Pd/C, 10 mg of cesium sulfate and 1 ml of 1,2-dimethoxyethane (hereinafter abbreviated to "DME"), the inside of the autoclave was thoroughly flushed with hydrogen, and then hydrogen pressure was arranged to 50 kg/cm$^2$G. Then the content was heated to 180° C. and maintained at that temperature for 16 hours to effect the hydrogenation reaction.

After the reaction, the autoclave was cooled to room temperature, hydrogen was purged and the liquid reaction product was recovered. The reaction product was filtered to remove the catalyst and cesium sulfate, and the filtrate was analyzed by the gas chromatography. The yield of γ-butyrolactone was 97.2% by mole based on the starting maleic anhydride. By-products such as tetrahydrofuran (hereinafter abbreviated to "THF") and 1,4-butanediol (hereinafter abbreviated to "1,4-BDO") were not found. The results are shown in Table 1.

EXAMPLES 2 to 6

The hydrogenation procedure of Example 1 was repeated wherein the alkali metal salts listed in Table 1 were used instead of cesium sulfate with all other conditions remaining substantially the same. The results are shown in Table 1.

EXAMPLE 7

Montmorillonite (KUNIPIA-G supplied by Kunipia Kogyo K.K.) was subjected to an ion exchange treatment with an aqueous potassium chloride solution to prepare K-type montmorillonite. The hydrogenation procedure of Example 1 was repeated wherein the thus-prepared K-type montmorillonite was used instead of cesium sulfate with all other conditions remaining substantially the same. The results are shown in Table 1.

EXAMPLE 8

The hydrogenation procedure of Example 1 was repeated wherein 116 mg (1 m-mol) of maleic acid was used instead of maleic anhydride with all other conditions remaining substantially the same. The results are shown in Table 1.

EXAMPLES 9 and 10

The hydrogenation procedure of Example 8 was repeated wherein the alkali metal salts listed in Table 1 were used instead of cesium chloride with all other conditions remaining substantially the same. The results are shown in Table 1.

EXAMPLES 11 and 12

The hydrogenation procedure of Example 1 was repeated wherein 100 mg (1 m-mol) of succinic anhydride (Example or 118 mg (1 m-mol) of succinic acid (Example 12) were used instead of maleic anhydride. All other conditions remained substantially the same. The results are shown in Table 1.

EXAMPLES 13

The hydrogenation procedure of Example 1 was repeated wherein THF was used as the solvent instead of DME with all other conditions remaining substantially the same. The results are shown in Table 1.

EXAMPLES 19 and 20

The hydrogenation procedure of Example 1 was repeated wherein the alkali metal salts listed in Table 2 were used instead of cesium sulfate and the reaction time was changed to 2 hours with all other conditions remaining substantially the same. The results are shown in Table 2.

EXAMPLE 21

The hydrogenation procedure of Example 1 was repeated wherein 116 mg (1 m-mol) of maleic acid was used instead of maleic anhydride and cesium acetate was used instead of cesium sulfate with all other conditions remaining substantially the same. The results are shown in Table 2.

EXAMPLES 22 and 23

The hydrogenation procedure of Example 1 was repeated wherein 100 mg (1 m-mol) of succinic anhydride (Example or 118 mg (1 m-mol) of succinic acid (Example 23) was used instead of maleic anhydride, and cesium acetate was used (Examples 22, 23) instead of cesium sulfate. All other conditions remained substantially the same. The results are shown in Table 2.

EXAMPLES 24

The hydrogenation procedure of Example 1 was repeated wherein THF was used as the solvent instead of DME and cesium acetate was used instead of cesium sulfate with all other conditions remaining substantially the same. The results are shown in Table 2.

TABLE 1

| Example No. | Starting compound | Solvent | Catalyst | Alkali metal salt | Reaction time (hr) | Yield of GBL (%) |
|---|---|---|---|---|---|---|
| 1 | MAN | DME | 5% Pd/C | $Cs_2SO_4$ | 16 | 97.2 |
| 2 | MAN | DME | 5% Pd/C | $Na_2SO_4$ | 16 | 85.7 |
| 3 | MAN | DME | 5% Pd/C | CsCl | 16 | 94.4 |
| 4 | MAN | DME | 5% Pd/C | $K_2SO_4$ | 16 | 92.9 |
| 5 | MAN | DME | 5% Pd/C | CsOH | 16 | 92.7 |
| 6 | MAN | DME | 5% Pd/C | $Rb_2CO_3$ | 16 | 90.8 |
| 7 | MAN | DME | 5% Pd/C | K-mont. | 16 | 82.8 |
| 8 | MAC | DME | 5% Pd/C | $Cs_2SO_4$ | 16 | 86.4 |
| 9 | MAC | DME | 5% Pd/C | $Na_2SO_4$ | 16 | 84.0 |
| 10 | MAC | DME | 5% Pd/C | $Rb_2CO_3$ | 16 | 86.8 |
| 11 | SAN | DME | 5% Pd/C | $Cs_2SO_4$ | 16 | 97.6 |
| 12 | SAC | DME | 5% Pd/C | $Cs_2SO_4$ | 16 | 88.1 |
| 13 | MAN | THF | 5% Pd/C | $Cs_2SO_4$ | 16 | 96.1 |

Note,
MAN: Maleic anhydride
SAN: Succinic anhydride
DME: 1,2-Dimethoxyethane
GBL: γ-Butyrolactone
MAC: Maleic acid
SAN: Succinic acid
THF: Tetrahydrofuran
K-mont.: K-tpye montomorillonite

EXAMPLES 14 to 18

The hydrogenation procedure of Example 1 was repeated wherein the alkali metal salts listed in Table 2 were used instead of cesium sulfate with all other conditions remaining substantially the same. The results are shown in Table 2.

TABLE 2

| Example No. | Starting compound | Solvent | Catalyst | Alkali metal salt | Reaction time (hr) | Yield of GBL (%) |
|---|---|---|---|---|---|---|
| 14 | MAN | DME | 5% Pd/C | $CH_3COOCs$ | 16 | 94.4 |

TABLE 2-continued

| Example No. | Starting compound | Solvent | Catalyst | Alkali metal salt | Reaction time (hr) | Yield of GBL (%) |
|---|---|---|---|---|---|---|
| 15 | MAN | DME | 5% Pd/C | CH₃COOLi | 16 | 80.6 |
| 16 | MAN | DME | 5% Pd/C | PhCOOCs | 16 | 92.1 |
| 17 | MAN | DME | 5% Pd/C | CH₃COOK | 16 | 90.3 |
| 18 | MAN | DME | 5% Pd/C | PhCOOK | 16 | 88.5 |
| 19 | MAN | DME | 5% Pd/C | BzSO₃Cs | 2 | 73.2 |
| 20 | MAN | DME | 5% Pd/C | p-Tol.SO₃Cs | 2 | 74.9 |
| 21 | MAC | DME | 5% Pd/C | CH₃COOCs | 16 | 83.1 |
| 22 | SAN | DME | 5% Pd/C | CH₃COOCs | 16 | 91.8 |
| 23 | SAC | DME | 5% Pd/C | CH₃COOCs | 16 | 95.2 |
| 24 | MAN | THF | 5% Pd/C | CH₃COOCs | 16 | 90.3 |

Note
MAN: Maleic anhydride
SAN: Succinic anhydride
DME: 1,2-dimethoxyethane
PhCOOCs: Cesium benzoate
BzSO₃Cs: Cesium benzenesulfonate
p-Tol.SO₃Cs: Cesium p-toluenesulfonate
GBL: γ-Butyrolactone

EXAMPLE 25

The procedure of hydrogenating maleic anhydride described in Example 1 was repeated wherein 10 mg of molecular sieve 3A (potassium-type A-zeolite supplied by Aldrich Chemical Co., Inc.) was used instead of cesium sulfate and the reaction time was changed to 4 hours. All other conditions remained substantially the same. The results are shown in Table 3.

Example 26

The hydrogenation procedure of Example 25 was repeated wherein 100 mg (1 m-mol) of succinic anhydride was used instead of maleic anhydride with all other conditions remaining substantially the same. The results are shown in Table 3.

EXAMPLES 27 and 28

The hydrogenation procedure of Example 1 was repeated wherein the alkali metal salts listed in Table 3 were used instead of cesium sulfate with all other conditions remaining substantially the same. The results are shown in Table 3.

EXAMPLE 29

A three-necked flask equipped with a reflux condenser was charged with 10 g of Na-type mordenite (TSZ640-NAA supplied by Tosoh Corp.), 21.8 g of potassium chloride and 150 ml of deionized water. The flask was maintained at 95° C. in a hot water bath for 5 hours to effect an ion exchange. The thus-obtained slurry was filtered, washed with water, dried at 110° C. overnight, and then calcined at 500° C. under an air stream for 3 hours to give potassium-type mordenite. The atomic ratio of potassium to aluminum (K/Al) was 0.98. The atomic ratio of sodium to aluminum (Na/Al) was 0.02.

The procedure of hydrogenating maleic anhydride described in Example I was repeated wherein the above-mentioned potassium-type mordenite was used instead of cesium sulfate with all other conditions remaining substantially the same. The results are shown in Table 3.

EXAMPLES 30 and 31

The hydrogenation procedure of Example 25 was repeated wherein 116 mg (1 m-mol) of maleic acid (Example 30) or 118 mg (1 m-mol) of succinic acid (Example 31) was used instead of maleic anhydride, and the reaction time was changed to 16 hours (Examples 30,31). All other conditions remained substantially the same. The results are shown in Table 3.

TABLE 3

| Example No. | Starting compound | Solvent | Catalyst | Alkali metal salt | Reaction time (hr) | Yield of GBL (%) |
|---|---|---|---|---|---|---|
| 25 | MAN | DME | 5% Pd/C | MS 3A | 4 | 99.0 |
| 26 | SAN | DME | 5% Pd/C | MS 3A | 4 | 99.0 |
| 27 | MAN | DME | 5% Pd/C | Na-mord. | 16 | 99.0 |
| 28 | MAN | DME | 5% Pd/C | Ferrierite | 16 | 96.2 |
| 29 | MAN | DME | 5% Pd/C | K-mord. | 16 | 92.7 |
| 30 | MAC | DME | 5% Pd/C | MS 3A | 16 | 99.0 |
| 31 | SAC | DME | 5% Pd/C | MS 3A | 16 | 99.0 |

Note
MAN: Maleic anhydride
MAC: Maleic acid

TABLE 3-continued

| Example No. | Starting compound | Solvent | Catalyst | Alkali metal salt | Reaction time (hr) | Yield of GBL (%) |
|---|---|---|---|---|---|---|

DME: 1,2-dimethoxyethane
Na-mord.: Na-type mordenite
K-mord.: K-type mordenite
SAN: Succinic anhydride
SAC: Succinic acid
GBL: γ-Butyrolactone
MS 3A: Molecular sieve 3A Comparative Example 1

The hydrogenation procedure of Example 1 was repeated wherein cesium sulfate was not used with all other conditions remaining substantially the same. The results are shown in Table 4.

Comparative Example 2

The hydrogenation procedure of Example 8 was repeated wherein cesium sulfate was not used with all other conditions remaining substantially the same. The results are shown in Table 4.

Comparative Examples 3 and 4

The hydrogenation procedure of Comparative Example was repeated wherein 100 mg (1 m-mol) of succinic anhydride (Comparative Example 3) or 118 mg (1 m-mol) of succinic acid (Comparative Example 4) was used instead of maleic anhydride. All other conditions remained substantially the same. The results are shown in Table 4.

Comparative Example 5

The hydrogenation procedure of Example I was repeated wherein cesium sulfate was not used and the reaction time was changed to 2 hours with all other conditions remaining substantially the same. The results are shown in Table 4.

resin. The resin was recovered by filtration and then dried at 105° C. for 24 hours to give a cesium-type cation exchange resin (cesium-type Amberlyst 16, ion exchange percentage: 82%).

A stainless steel autoclave having a volume of 10 ml was charged with 98 mg (1 m-mol) of maleic anhydride, 21 mg of 5% Pd/C, 20 mg of cesium-type Amberlyst 16 (ion exchange percentage: 82%) and 1 ml of DME, the inside of the autoclave was thoroughly flushed with hydrogen, and then the hydrogen pressure was arranged to 50 kg/cm$^2$G. Then the content was heated to 120° C. and maintained at that temperature for 16 hours to effect the hydrogenation reaction.

After the reaction, the autoclave was cooled to room temperature, hydrogen was purged and the liquid reaction product was recovered. The reaction product was filtered to remove the catalyst and the resin, and the filtrate was analyzed by the gas chromatography.

The yield of y-butyrolactone was 56.6% by mole based on the starting maleic anhydride.

Example 33

Following substantially the same ion exchange procedure as that described in Example 32, potassium-type Amberlyst 16 (ion exchange percentage: 88%) was prepared instead of the cessium-type strongly acidic cation exchange material.

TABLE 4

| Comparative Example No. | Starting Compound | Solvent | Catalyst | Alkali metal salt | Reaction time (hr) | Yield of GBL (%) |
|---|---|---|---|---|---|---|
| 1 | MAN | DME | 5% Pd/C | — | 16 | 75.8 |
| 2 | MAC | DME | 5% Pd/C | — | 16 | 65.6 |
| 3 | SAN | DME | 5% Pd/C | — | 16 | 74.7 |
| 4 | SAC | DME | 5% Pd/C | — | 16 | 48.0 |
| 5 | MAN | DME | 5% Pd/C | — | 2 | 69.0 |

Note
MAN: Maleic anhydride
MAC: Maleic acid
DME: 1,2-dimethoxyethane
SAN: Succinic anhydride
SAC: Succinic acid
GBL: γ-Butyrolacotne

EXAMPLE 32

A glass column was charged with 10 ml of a proton-type strongly acidic cation exchange resin (Amberlyst 16 Wet supplied by Organo Corporation). Through the column, 100 ml of deionized water was allowed to flow to effect prewashing of the resin. Then 50 ml of 1N cesium chloride was allowed to flow at a space velocity of 6/h to 7/h to effect an ion exchange and thereafter deionized water was allowed to flow at a space velocity of 20/h for 30 minutes to wash the The hydrogenation procedure of Example 32 was repeated wherein the potassium-type Amberlyst 16 was used instead of the cesium-type strongly acidic cation exchange resin. All other conditions remained substantially the same. The results are shown in Table 5.

Example 34

A stainless steel autoclave equipped with an electromagnetic stirrer and having a volume of 200 ml was charged with 2.94 g (30 m-mol) of maleic anhydride, 0.64 g of 5% Pd/C, 600 mg of potassium-type weakly acidic cation exchange resin (potassium-type IRC-50) and 30 ml of DME, the inside of the autoclave was thoroughly flushed with hydrogen, and then the hydrogen pressure was arranged to 100 kg/cm$^2$G. Then the content was heated to 120° C. with stirring and maintained at that temperature for 5 hours to effect the hydrogenation reaction.

After the reaction, the autoclave was cooled to room temperature, hydrogen as purged and the liquid reaction product was recovered. The reaction product was filtered to remove the palladium catalyst and the ion exchange resin, and the filtrate was analyzed by the gas chromatography. The yield of γ-butyrolactone was 99.9% by mole based on the starting maleic anhydride. By-products such as THF and 1,4-BDO were not found. The results are shown in Table 5.

EXAMPLE 35

By substantially the same procedure as described in Example 34, hydrogenation of maleic anhydride was carried out wherein the palladium catalyst and the ion exchange resin which were recovered by filtration of the liquid reaction product obtained in Example 34 were used. This hydrogenation procedure was repeated 8 times. In each of the eight hydrogenation procedures, the palladium catalyst and the ion exchange resin, which were recovered by filtration of the liquid reaction product obtained in the previous hydrogenation procedure, were used with all other conditions remaining substantially the same. The yield of γ-butyrolactone was higher than 98% by mole based on the starting maleic anhydride in each of the repeated procedures. By-products such as THF and 1,4-BDO were not found in each reaction product.

Comparative Example 6

The hydrogenation procedure of Example 32 was repeated wherein the cesium-type strongly acidic cation exchange resin was not used with all other conditions remaining substantially the same. The results are shown in Table 5.

Comparative Example 7

The hydrogenation procedure of Example 34 was repeated wherein the potassium-type strongly acidic cation exchange resin was not used with all other conditions remaining substantially the same. The results are shown in Table 5.

EXAMPLE 36

The hydrogenation procedure of Example 1 was repeated wherein 10 mg of potassium maleate was used instead of cesium sulfate with all other conditions remaining substantially the same. The results are shown in Table 6.

EXAMPLES 37 to 46

The hydrogenation procedure of Example 36 was repeated wherein each of the alkali metal salts listed in Table 6 was used instead of potassium maleate and the reaction time was changed to 2 hours. All other conditions remained substantially the same. The results are shown in Table 6.

EXAMPLE 47

The hydrogenation procedure of Example 36 was repeated wherein 116 mg (1 m-mol) of maleic acid was used instead of maleic anhydride with all other conditions remaining substantially the same. The results are shown in Table 6.

The yield of γ-butyrolactone was 85.8% by mole based on the starting maleic acid. By-products such as THF and 1,4-BDO were not found. The results are shown in Table 6.

EXAMPLE 48

The hydrogenation procedure of Example 47 was repeated wherein cesium maleate was used instead of potassium maleate and the reaction time was changed to 2 hours with all other conditions remaining substantially the same. The results are shown in Table 6.

EXAMPLES 49 and 50

The hydrogenation procedure of Example 37 was repeated wherein 100 mg (1 m-mol) of succinic anhydride (Example 49) or 118 mg (1 m-mol) of succinic acid (Example 50) was used instead of maleic anhydride with all other conditions substantially the same. The results are shown in Table 6.

EXAMPLE 51

The hydrogenation procedure of Example 37 was repeated wherein THF was used instead of DME with all other conditions remaining substantially the same. The results are shown in Table 6.

TABLE 5

| Example & Comparative Example No. | Starting compound | Solvent | Catalyst | Alkali metal salt | Reaction time (hr) | Pressure (kg/cm$^2$) | Yield of GBL (%) |
| --- | --- | --- | --- | --- | --- | --- | --- |
| Ex. 32 | MAN | DME | 5% Pd/C | Cs-Am | 16 | 50 | 56.6 |
| Ex. 33 | MAN | DME | 5% Pd/C | K-Am | 16 | 50 | 68.7 |
| Ex. 34 | MAN | DME | 5% Pd/C | K-IRC | 5 | 100 | 99.9 |
| Com. 6 | MAN | DME | 5% Pd/C | — | 16 | 50 | 3.3 |
| Com. 7 | MAN | DME | 5% Pd/C | — | 5 | 100 | 84.5 |

Note
MAN: Maleic anhydride
GBL: γ-Butyrolactone
Cs-Am: Cs-Amberlist 16
DME: 1,2-dimethoxyethane
K-Am: K-Amberlyst 16
K-IRC: K-IRC-50

TABLE 6

| Example No. | Starting compound | Solvent | Catalyst | Alkali metal salt | Reaction time (hr) | Yield of GBL (%) |
|---|---|---|---|---|---|---|
| 36 | MAN | DME | 5% Pd/C | K-maleate | 16 | 91.9 |
| 37 | MAN | DME | 5% Pd/C | Cs-maleate | 2 | 92.6 |
| 38 | MAN | DME | 5% Pd/C | Cs-succinate | 2 | 85.5 |
| 39 | MAN | DME | 5% Pd/C | Cs-malonate | 2 | 87.4 |
| 40 | MAN | DME | 5% Pd/C | Cs-glutarate | 2 | 89.8 |
| 41 | MAN | DME | 5% Pd/C | Cs-Et-maleate | 2 | 85.5 |
| 42 | MAN | DME | 5% Pd/C | Cs-Et-succinate | 2 | 86.9 |
| 43 | MAN | DME | 5% Pd/C | Cs-isophthalate | 2 | 96.1 |
| 44 | MAN | DME | 5% Pd/C | Cs-OH-butyrate | 2 | 91.8 |
| 45 | MAN | DME | 5% Pd/C | Cs-F-propionate | 2 | 83.6 |
| 46 | MAN | DME | 5% Pd/C | Cs-S-salycylate | 2 | 84.4 |
| 47 | MAC | DME | 5% Pd/C | K-maleate | 16 | 85.8 |
| 48 | MAC | DME | 5% Pd/C | Cs-maleate | 2 | 80.3 |
| 49 | SAN | DME | 5% Pd/C | Cs-maleate | 2 | 89.3 |
| 50 | SAC | DME | 5% Pd/C | Cs-maleate | 2 | 92.1 |
| 51 | MAN | THF | 5% Pd/C | Cs-maleate | 2 | 84.9 |

Note
MAN: Maleic anhydride
SAN: Succinic anhydride
DME: 1,2-Dimethoxyethane
GBL: γ-Butyrolactone
MAC: Maleic acid
SAC: Succinic acid
THF: Tetrahydrofuran
Cs-maleate: Cesium maleate
Cs-Et-maleate: Cesium monoethyl maleate
Cs-Et-succinate: Cesium monoethyl succinate
Cs-OH-butyrate: Cesium 4-hydroxy-butyrate
Cs-F-propionate: Cesium 3-formylpropionate
Cs-S-salycylate: Cesium 5-sulfosalycylate
K-maleate: Potassium maleate
Cs-succinate: Cesium succinate
Cs-malonate: Cesium malonate
Cs-glutarate: Cesium glutarate
Cs-isophthalate: Cesium isophthalate
K-maleate: Ptassim maleate

EXAMPLE 52

In 10 ml of 4N hydrochloric acid, 0.15 g of palladium chloride ($PdCl_2$, supplied by N. E. CHEMCAT Corporation) was dissolved. Into this solution, 2.85 g of powdery silica having a particle diameter below 200 mesh (CARiACT 15, supplied by Fuji-Davison Chemical Ltd.) was added. Water was removed from the solution under a reduced pressure by using a rotary evaporator, and the paste obtained was dried under a reduced pressure at 80° C. for 2 hours and further at 110° C. for 2 hours. Thus-obtained catalyst precursor was introduced into a tubular glass, and was reduced under the flow of a mixed gas composed of 135 ml/min of nitrigen and 15 ml/min of hydrogen at 400° C. for 2 hours to give a 5% Pd/silica catalyst.

In 3 ml of deionized water, 0.016 g of lead nitrate ($Pb(NO_3)_2$, supplied by Wako Junyaku K.K.) was dissolved. To this solution, 1.00 g of the above-mentioned 5% Pd/silica catalyst. Water was removed from the solution under a reduced pressure by using a rotary evaporator, and the paste obtained was dried at 120° C. under normal pressure for 3 hours. Thus-obtained catalyst precursor was introduced into a tubular glass, and was reduced under the flow of a mixed gas composed of 135 ml/min of nitrigen and 15 ml/min of hydrogen at 200° C. for one hour to give a Pb/Pd/silica catalyst.

A stainless steel autoclave having a volume of 10 ml was charged with 98 mg (1 m-mol) of maleic anhydride, 21 mg of the above-mentioned Pb/Pd/silica catalyst, 10 mg of cesium carbonate and 1 ml of DME, the inside of the autoclave was thoroughly flushed with hydrogen, and then, hydrogen pressure was arranged to 50 kg/cm²G. Then the content was heated to 180° C. with stirring and maintained at that temperature for 2 hours to effect the hydrogenation reaction.

After the reaction, the autoclave was cooled to room temperature, hydrogen was purged and the liquid reaction product was recovered. The reaction product was filtered to remove the catalyst and cesium carbonate, and the filtrate was analyzed by the gas chromatography. The yield of γ-butyrolaotone was 94.3% by mole based on the Starting maleic anhydride. By-products such as propionic acid, 1,4-BDO and THF were not found. The results are shown in Table 7.

EXAMPLE 53

The hydrogenation procedure of Example 52 was repeated wherein cesium monosuccinate was used instead of cesium carbonate with all other conditions remaining substantially the same. The results are shown in Table 7.

EXAMPLE 54

The hydrogenation procedure of Example 52 was repeated wherein molecular sieve 3A (potassium-type A-zeolite) was used instead of cesium carbonate with all other conditions remaining substantially the same. The results are shown in Table 7.

Comparative Example 8

The hydrogenation procedure of Example 52 was repeated wherein the cesium carbonate was not used with all other conditions remaining substantially the same. The results are shown in Table 7.

TABLE 7

| Example No. | Starting compound | Solvent | Catalyst | Alkali metal salt | Readtion time (hr) | Yield of GBL (%) |
|---|---|---|---|---|---|---|
| 52 | MAN | DME | Pb/Pd/silica | Cs-carbonate | 2 | 94.3 |
| 53 | MAN | DME | Pb/Pd/silica | Cs-m-suc. | 2 | 90.8 |
| 54 | MAN | DME | Pb/Pd/silica | MS 3A | 2 | 98.4 |
| Comp. 8 | MAN | DME | Pb/Pd/silica | — | 2 | 86.1 |

Note
MAN: Maleic anhydride
GBL: γ-Butyrolactone
Cs-m-suc.: Cesium monosuccinate
DME: Dimethoxyethane
MS 3A: Molecular sieve 3A Example 55

In 10 ml of deionized water, 1.49 g of nickel nitrate (Ni(NO$_3$)$_2$.6H$_2$O) was dissolved. Into this solution, 2.72 g of powdery silica having a particle diameter below 200 mesh (CARiACT 10, supplied by Fuji-Davison Chemical Ltd.) was added. Water was removed from the solution under a reduced pressure by using a rotary evaporator, and the paste obtained was dried under a reduced pressure at 80° C. for 2 hours and further at 110° C. for 2 hours. Thus-obtained catalyst precursor was introduced into a tubular glass, and was reduced under the flow of a mixed gas composed of 100 ml/min of nitrogen and 10 ml/min of hydrogen at 400° C. for 2 hours to give a 10% Ni/silica catalyst.

A stainless steel autoclave having a volume of 10 ml was charged with 98 mg (1 m-mol) of maleic anhydride, 21 mg of the above-mentioned 10% Ni/silica catalyst, 10 mg of molecular sieve 3A (potassium-type A-zeolite) and 1 ml of DME, the inside of the autoclave was thoroughly flushed with hydrogen, and then, hydrogen pressure was arranged to 50 kg/cm$^2$G. Then the content was heated to 180° C. with stirring and maintained at that temperature for 2 hours to effect the hydrogenation reaction.

After the reaction, the autoclave was cooled to room temperature, hydrogen was purged and the liquid reaction product was recovered. The reaction product was filtered to remove the catalyst and molecular sieve 3A, and the filtrate was analyzed by the gas chromatography. The yield of γ-butyrolactone was 80.0% by mole based on the starting maleic anhydride. The results are shown in Table 8.

Example 56 to 61

The hydrogenation procedure of Example 55 was repeated wherein the alkali metal salts shown in Table 8 were used instead of molecular sieve 3A with all other conditions remaining substantially the same. The results are shown in Table 8.

EXAMPLE 62

Following substantially the same procedure as described in Example 55, a 10% Ni/diatomaceous earth catalyst was prepared by using diatomaceous earth instead of silica.

The hydrogenation procedure of Example 55 was repeated wherein the above-mentioned 10% Ni/diatomaceous catalyst was used instead of 10% Ni/silica catalyst with all other conditions remaining substantially the same. The results are shown in Table 8.

EXAMPLE 63

The hydrogenation procedure of Example 58 was repeated wherein 100 mg (1 m-mol) of succinic anhydride was used instead of maleic anhydride with all other conditions remaining substantially the same. The results are shown in Table 8.

Example 64

The hydrogenation procedure of Example 55 was repeated wherein THF was used instead of DME, and cesium maleate was used instead of molecular sieve 3A. All other conditions remained substantially the same. The results are shown in Table 8.

TABLE 8

| Example No. | Starting compound | Solvent | Catalyst | Alkali metal salt | Reaction time (hr) | Yield of GBL (%) |
|---|---|---|---|---|---|---|
| 55 | MAN | DME | 10% Ni/Si | MS-3A | 2 | 80.0 |
| 56 | MAN | DME | 10% Ni/Si | Cs carbonate | 2 | 75.6 |
| 57 | MAN | DME | 10% Ni/Si | P-Tol.SO$_3$Cs | 2 | 72.0 |
| 58 | MAN | DME | 10% Ni/Si | Cs succinate | 2 | 78.8 |
| 59 | MAN | DME | 10% Ni/Si | Cs acetate | 2 | 75.3 |
| 60 | MAN | DME | 10% Ni/Si | Cs benzoate | 2 | 80.2 |
| 61 | MAN | DME | 10% Ni/Si | K maleate | 2 | 82.6 |
| 62 | MAN | DME | 10% Ni/Di | MS-3A | 2 | 37.0 |
| 63 | SAN | DME | 10% Ni/Si | Cs succinate | 2 | 74.5 |
| 64 | MAN | THF | 10% Ni/Si | Cs maleate | 2 | 79.4 |

Note

TABLE 8-continued

| Example No. | Starting compound | Solvent | Catalyst | Alkali metal salt | Reaction time (hr) | Yield of GBL (%) |
| --- | --- | --- | --- | --- | --- | --- |

MAN: Maleic anhydride
DME: 1,2-Dimethoxyethane
GBL: γ-Butyrolactone
10% Ni/Si: 10% Ni/silica
10% Ni/Di: 10% Ni/diatomaceous earth
MS-3A: Molecular sieve 3A
p-Tol.SO$_3$Cs: Cesium p-toluenesulfonate

EXAMPLE 65

In an aqueous 10% ammonia solution, 1.49 g of nickel nitrate (Ni(NO$_3$)$_2$.6H$_2$O) and 0.12 g of palladium acetate were dissolved. Into this solution, 2.72 g of powdery silica having a particle diameter below 200 mesh (CARiACT 10, supplied by Fuji-Davison Chemical Ltd.) was added. The solution was allowed to stand for a predetermined period and then water was removed from the solution under a reduced pressure by using a rotary evaporator. The paste obtained was dried under a reduced pressure at 80° C. for 2 hours and further at 110° C. for 2 hours. Thus-obtained catalyst precursor was introduced into a tubular glass, and was reduced under the flow of a mixed gas composed of 100 ml/min of nitrogen and 10 ml/min of hydrogen at 400° C. for 2 hours to give a 10% Ni-Pd/silica catalyst.

A stainless steel autoclave having a volume of 10 ml was charged with 98 mg (1 m-mol) of maleic anhydride, 21 mg of the above-mentioned 10% Ni-Pd/silica catalyst, 10 mg of cesium sulfate and 1 ml of DME, the inside of the autoclave was thoroughly flushed with hydrogen, and then, the hydrogen pressure was arranged to 50 kg/cm$^2$G. Then the content was heated to 180° C. with stirring and maintained at that temperature for 2 hours to effect the hydrogenation reaction.

After the reaction, the autoclave was cooled to room temperature, hydrogen was purged and the liquid reaction product was recovered. The reaction product was filtered to remove the catalyst and cesium sulfate, and the filtrate was analyzed by the gas chromatography. The yield of γ-butyrolactone was 92.9% by mole based on the starting maleic anhydride. The results are shown in Table 9.

EXAMPLES 66 to 70

The hydrogenation procedure of Example 65 was repeated wherein each of the raw materials shown in Table 9 was used in an amount of 1 m-mol and each of the alkali metal salts shown in Table 9 was used. All other conditions remained substantially the same. The results are shown in Table 9.

EXAMPLE 71

In deionized water, 1.49 g of nickel nitrate (Ni(NO$_3$)$_2$.6H$_2$O) and 0.13 g of perrhenic acid were dissolved. To this solution, 2.72 g of powdery silica having a particle diameter below 200 mesh (CARiACT 10, supplied by Fuji-Davison Chemical Ltd.) was added. The solution was allowed to stand for a predetermined period and then water was removed from the solution under a reduced pressure by using a rotary evaporator. The paste obtained was dried under a reduced pressure at 80° C. for 2 hours and further at 110° C. for 2 hours. Thus-obtained catalyst precursor was introduced into a tubular glass, and was reduced under the flow of a mixed gas composed of 100 ml/min of nitrogen and 10 ml/min of hydrogen at 400° C. for 2 hours to give a Ni-Re/silica catalyst.

A stainless steel autoclave having a volume of 10 ml was charged with 98 mg (1 m-mol) of maleic anhydride, 21 mg of the above-mentioned Ni-Re/silica catalyst, 10 mg of cesium sulfate and 1 ml of DME, the inside of the autoclave was thoroughly flushed with hydrogen, and then, the hydrogen pressure was arranged to 50 kg/cm$^2$G. Then the content was heated to 180° C. with stirring and maintained at that temperature for 2 hours to effect the hydrogenation reaction.

After the reaction, the autoclave was cooled to room temperature, hydrogen was purged and the liquid reaction product was recovered. The reaction product was filtered to remove the catalyst and cesium sulfate, and the filtrate was analyzed by the gas chromatography. The yield of γ-butyrolactone was 79.3% by mole based on the starting maleic anhydride. By-products such as THF and 1,4-BDO were not found. The results are shown in Table 9.

EXAMPLES 72 to 74

The hydrogenation procedure of Example 71 was repeated wherein each of the raw materials shown in Table 9 was used in an amount of 1 m-mol and each of the alkali metal salts shown in Table 9 was used. All other conditions remained substantially the same. The results are shown in Table 9.

EXAMPLE 75

Following substantially the same procedure as described in Example 71, an Ni-Mo/silica catalyst was prepared wherein the amount of nickel nitrate (Ni(NO$_3$)$_2$ 6H$_2$O) was changed to 1,52 g and 0.63 g of ammonium molybdate was used instead of perrhenic acid.

The hydrogenation procedure of Example 71 was repeated wherein the above-mentioned Ni-Mo/silica catalyst was used instead of the Ni-Re/silica catalyst and cesium carbonate was used instead of cesium sulfate. All other conditions remained substantially the same. The results are shown in Table 9.

EXAMPLE 76

In deionized water, 3.45 g of cobalt nitrate (Co(NO$_3$)$_2$ 6H$_2$O) and 0.15 g of palladium nitrate were dissolved. To this solution, 2.72 g of diatomaceous earth was added. The solution was allowed to stand for 12 hours, and then water was removed from the solution under a reduced pressure by using a rotary evaporator. The paste obtained was dried under a reduced pressure at 80° C. for 2 hours and further at 110° C. for 2 hours. Thus-obtained catalyst precursor was introduced into a tubular glass, and was reduced under the flow of a mixed gas composed of 100 ml/min of nitrogen and 10 ml/min of hydrogen at 400° C. for 2 hours to give a Co-Pd/diatomaceous earth catalyst.

A stainless steel autoclave having a volume of 10 ml was charged with 98 mg (1 m-mol) of maleic anhydride, 21 mg of the above-mentioned Co-Pd/diatomaceous earth catalyst, 10 mg of molecular sieve 3A (potassium-type A-zeolite, supplied by Aldrich Chemical Co., Ltd.) and 1 ml of DME, the inside of the autoclave was thoroughly flushed with hydrogen, and then, the hydrogen pressure was arranged to 50 kg/cm$^2$G. Then the content was heated to 180° C. with stirring and maintained at that temperature for 2 hours to effect the hydrogenation reaction.

After the reaction, the autoclave was cooled to room temperature, hydrogen was purged and the liquid reaction product was recovered. The reaction product was filtered to remove the catalyst and the molecular sieve, and the filtrate was analyzed by the gas chromatography. The yield of γ-butyrolactone was 42.0% by mole based on the starting maleic anhydride. By-products such as THF and 1,4-BDO were not found. The results are shown in Table 9.

TABLE 9

| Example No. | Starting compound | Solvent | Catalyst | Alkali metal salt | Reaction time (hr) | Yield of GBL (%) |
|---|---|---|---|---|---|---|
| 65 | MAN | DME | Ni—Pd/Si | Cs sulfate | 2 | 92.9 |
| 66 | MAN | DME | Ni—Pd/Si | Cs carbonate | 2 | 84.2 |
| 67 | MAN | DME | Ni—Pd/Si | MS-3A | 2 | 83.4 |
| 68 | SAN | DME | Ni—Pd/Si | Cs sulfate | 2 | 92.6 |
| 69 | SAN | DME | Ni—Pd/Si | Cs succinate | 2 | 85.2 |
| 70 | SAN | DME | Ni—Pd/Si | K sulfate | 2 | 88.0 |
| 71 | MAN | DME | Ni—Re/Si | Cs sulfate | 2 | 79.3 |
| 72 | MAN | DME | Ni—Re/Si | K sulfate | 2 | 82.1 |
| 73 | SAN | DHE | Ni—Re/Si | Cs sulfate | 2 | 89.7 |
| 74 | SAN | DME | Ni—Re/Si | K sulfate | 2 | 81.3 |
| 75 | MAN | DME | Ni—Mo/Si | Cs carbonate | 2 | 51.6 |
| 76 | MAN | DME | Co—Pd/Di | MS-3A | 2 | 42.0 |

Note
MAN: Maleic anhydride
DME: 1,2-Dimethoxyethane
Ni—Pd/Si: Ni—Pd/silica
Ni—Mo/Si: Ni—Mo/silica
Co—Pd/Di: Co—Pd/diatomaceous earth
MS-3A: Molecular sieve 3A
SAN: Succinic anhydride
GBL: γ-Butyrolactone
Ni—Re/Si: Ni—Re/silica Comparative Example 9

The hydrogenation procedure of Example 55 was repeated wherein the molecular sieve 3A was not used with all other conditions remaining substantially the same. The results are shown in Table 10.

Comparative Example 10

The hydrogenation procedure of Example 55 was repeated wherein 10% Ni/diatomaceous earth catalyst was used instead of the 10% Ni/silica catalyst, and the alkali metal salt was not used. All other conditions remained substantially the same. The results are shown in Table 10.

Comparative Example 11

The hydrogenation procedure of Example 55 was repeated wherein succinic anhydride was used instead of the maleic anhydride and the alkali metal salt was not used. All other conditions remained substantially the same. The results are shown in Table 10.

Comparative Example 12

The hydrogenation procedure of Example 55 was repeated wherein THF was used instead of DME and the alkali metal salt was not used with all other conditions remaining substantially the same. The results are shown in Table 10.

Comparative Example 13

The hydrogenation procedure of Example 65 was repeated wherein the cesium sulfate was not used with all other conditions remaining substantially the same. The results are shown in Table 10.

Comparative Example 14

The hydrogenation procedure of Example 65 was repeated wherein the raw material was changed to succinic anhydride and the alkali metal salt was not used with all other conditions remaining substantially the same. The results are shown in Table 10.

Comparative Example 15

The hydrogenation procedure of Example 71 was repeated wherein the cesium sulfate was not used with all other conditions remaining substantially the same. The results are shown in Table 10.

Comparative Example 16

The hydrogenation procedure of Example 71 was repeated wherein the raw material was changed to succinic anhydride and the alkali metal salt was not used with all other conditions remaining substantially the same. The results are shown in Table 10.

Comparative Example 17

The hydrogenation procedure of Example 75 was repeated wherein the cesium carbonate was not used with all other conditions remaining substantially the same. The results are shown in Table 10.

Comparative Example 18

The hydrogenation procedure of Example 76 was repeated wherein the molecular sieve 3A was not used with all other conditions remaining substantially the same. The results are shown in Table 10.

TABLE 10

| Comp. Example No. | Starting compound | Solvent | Catalyst | Alkali metal salt | Reaction time (hr) | Yield of GBL (%) |
|---|---|---|---|---|---|---|
| 9 | MAN | DME | 10% Ni/Si | — | 2 | 63.8 |
| 10 | MAN | DME | 10% Ni/Di | — | 2 | 26.5 |
| 11 | SAN | DME | 10% Ni/Si | — | 2 | 62.0 |
| 12 | MAN | THF | 10% Ni/Si | — | 2 | 59.3 |
| 13 | MAN | DME | Ni—Pd/Si | — | 2 | 80.1 |
| 14 | SAN | DME | Ni—Pd/Si | — | 2 | 82.8 |
| 15 | MAN | DME | Ni—Re/Si | — | 2 | 71.8 |
| 16 | SAN | DME | Ni—Re/Si | — | 2 | 79.0 |
| 17 | MAN | DME | Ni—Mo/Si | — | 2 | 47.0 |
| 18 | MAN | DME | Co—Pd/Di | — | 2 | 13.5 |

Note
MAN: Maleic anhydride
DME: 1,2-Dimethoxyethane
10% Ni/Si: 10% Ni/silica
Ni—Re/Si: Ni—Re/silica
Co—Pd/Di: Co—Pd/diatomaceous earth
THF: Tetrahydrofuran

What is claimed is:

1. A process for the preparation of a γ-lactone which comprises catalytically hydrogenating at least one compound selected from the group consisting of dicarboxylic acids having a maleic acid core structure or a succinic acid core structure and having 4 to 10 carbon atoms, or functional derivatives thereof, in the presence of a catalyst comprising at least one metal selected from the group consisting of ruthenium, rhodium, palladium, iridium and platinum or a combination of said metals with at least one element selected from the group consisting of the elements of Group IVa, VIb and VIIb of the periodic table, and there is also added to the reaction mixture, in addition to and apart from the catalyst, at least one compound selected from the group consisting of alkali metal salts and alkali metal hydroxides.

2. The process according to claim 1, wherein said catalytic hydrogenation is carried out at a temperature of from room temperature to 300° C. and a pressure of 10 to 200 kg/cm²G.

3. The process according to claim 1, wherein said functional derivatives of the dicarboxylic acids are anhydrides of the dicarboxylic acids.

4. The process according to claim 1, wherein said dicarboxylic acids are selected from the group consisting of maleic acid and succinic acid and said functional derivatives of the dicarboxylic acids are selected from the group consisting of maleic anhydride and succinic anhydride.

5. The process according to claim 1, wherein said γ-lactone is γ-butyrolactone.

6. The process according to claim 1, wherein said elements of groups IVa, VIb and VIIb of the periodic table are selected from the group consisting of lead, molybdenum and rhenium.

7. The process according to claim 1, wherein the atomic ratio of said metal selected from ruthenium, rhodium, palladium, iridium and platinum to the element selected from the groups IVa, IVb and VIIb is the range of from 200/1 to 1/50.

8. The process according to claim 1, wherein the amount of the catalyst is 0.5 to 200% by weight based on the weight of the compound selected from the dicarboxylic acids and the functional derivatives.

9. The process according to claim 1, wherein said alkali metal salt is selected from the group consisting of alkali-type zeolites, inorganic alkali metal salts, alkali metal salts of a monofunctional organic compound, alkali metal-substituted organic cation exchange materials, and alkali metal salts of an organic compound having at least two functional groups.

10. The process according to claim 1, wherein the cation of said alkali metal salts is selected from the group consisting of lithium, sodium, potassium, rubidium and cesium.

11. The process according to claim 10, wherein said alkali-type zeolites are selected from the group consisting of erionite, ofretite, erionite-ofretite, gmelinite, mazzite, mordenite, ferrierite, A-type zeolite, X-type zeolite, Y-type zeolite, USY-type zeolite, L-type zeolite and ZSM-5-type zeolite, which have at least one ion-exchangeable alkali cation selected from the group consisting of lithium, sodium, potassium, rubidium and cesium.

12. The process according to claim 9, wherein said inorganic alkali metal salts are selected from the group consisting of a chloride, nitrate, carbonate, sulfate, phosphate and hydroxide of an alkali metal, and alkali metal-type montmorillonite and alkali metal-type kaolinite.

13. The process according to claim 9, wherein said alkali metal salts of a monofunctional organic compound are monofunctional aliphatic organic acid salts or monofunctional aromatic organic acid salts.

14. The process according to claim 13, wherein said monofunctional aliphatic organic acid salts are selected from the group consisting of an acetate, trifluoroacetate, propionate and methylsulfonate of an alkali metal.

15. The process according to claim 13, wherein said monofunctional aromatic organic acid salts are selected from the group consisting of a benzoate, benzenesulfonate and p-toluenesulfonate of an alkali metal.

16. The process according to claim 9, wherein said alkali metal-substituted organic cation exchange materials are selected from the group consisting of ion exchange resins, ion exchange fibers and ion exchange membranes, which are made of a methacrylic acid-divinylbenzene copolymer, an acrylic acid-divinylbenzene copolymer, a styrene-divinylbenzene copolymer having at least one functional group selected from a sulfonic acid group, a carboxyl group, a phosphonic acid group, a phosphinic acid group and an arsenic acid group, a phenol-formaldehyde copolymer having at least one functional group selected from a sulfonic acid group, a carboxyl group, a phosphonic acid group, a phosphinic acid group and an arsenic acid group, or a perfluorovinyl ether-tetrafluoroethylene copolymer.

17. The process according to claim 9, wherein said alkali metal salts of an organic compound having at least two functional groups are selected from the group consisting of alkali metal salts of an aliphatic or aromatic compound which has as one of the functional groups a carboxyl group or a sulfonic acid group and further has as the other functional group or groups at least one functional group selected from the group consisting of a hydroxyl group, a carboxyl group, an alkoxycarbonyl group having 1 to 10 carbon atoms in the alkyl group, a formyl group, a sulfonic acid group and an amino group.

18. The process according to claim 1, wherein the amount of said compound selected from alkali metal salts and alkali metal hydroxides is from 0.1 to 100% by weight based on the weight of the compound selected from the dicarboxylic acids having 4 to 10 carbon atoms and the functional derivatives thereof.

19. The process according to claim 1, wherein said catalyst is supported on a carrier.

20. The process according to claim 19, wherein the amount of said metal selected from ruthenium, rhodium, palladium, iridium and platinum is 0.1 to 60% by weight based on the total weight of the catalyst comprising said metal and the carrier.

21. The process according to claim 19, wherein said carrier is selected from the group consisting of crystalline and non-crystalline metal oxides and double oxides.

22. The process according to claim 21, wherein the crystalline and non-crystalline metal oxides and double oxides are selected from the group consisting of silica, alumina, titania, silica-alumina, zeolites and diatomaceous earth.

23. The process according to claim 19, wherein said carrier is activated carbon.

24. The process according to claim 19, wherein said carrier is a clay compound.

25. The process according to claim 24, wherein said clay compound is selected from the group consisting of teniorite, hectorite, montmorillonite and bentonite.

26. The process according to claim 1, wherein the amount of said compound selected from alkali metal salts and alkali metal hydroxides is from 1 to 50% by weight based on the weight of the compound selected from the dicarboxylic acids having 4 to 10 carbon atoms or its functional derivatives.

27. The process according to claim 1, wherein said metal is palladium.

* * * * *